(12) United States Patent
Graham et al.

(10) Patent No.: US 8,603,804 B2
(45) Date of Patent: Dec. 10, 2013

(54) FLUORESCENT MARKED MICROSCOPE SLIDE

(75) Inventors: Christopher J. Graham, Frenchville, PA (US); Craig Stout, Port Matilda, PA (US)

(73) Assignee: QBC Diagnostics, Inc., Port Matilda, PA (US)

( * ) Notice: Subject to any disclaimer, the term of this patent is extended or adjusted under 35 U.S.C. 154(b) by 367 days.

(21) Appl. No.: 12/930,306

(22) Filed: Jan. 3, 2011

(65) Prior Publication Data

US 2011/0177548 A1    Jul. 21, 2011

Related U.S. Application Data

(60) Provisional application No. 61/336,115, filed on Jan. 15, 2010.

(51) Int. Cl.
  *C12M 1/34*  (2006.01)
(52) U.S. Cl.
  USPC ..................... 435/288.3; 435/288.7
(58) Field of Classification Search
  USPC ........................... 435/288.3, 288.7
  See application file for complete search history.

(56) References Cited

U.S. PATENT DOCUMENTS

| | | |
|---|---|---|
| 4,190,314 A | 2/1980 | Goldsmith |
| 4,741,043 A | 4/1988 | Bacus |
| 5,812,312 A | 9/1998 | Lorincz |
| 5,866,331 A | 2/1999 | Singer |
| 6,431,007 B1 | 8/2002 | Roy |
| 6,567,214 B2 | 5/2003 | Lorincz |
| 2009/0238435 A1 | 9/2009 | Shields |
| 2010/0231703 A1 | 9/2010 | Varga et al. |

FOREIGN PATENT DOCUMENTS

| | | |
|---|---|---|
| EP | 02103925 | 9/2009 |
| EP | 02024772 | 12/2009 |
| WO | WO97-14816 | 4/1997 |
| WO | WO2007-138369 | 12/2007 |

OTHER PUBLICATIONS

Walker et al. "Permanent fluorescent test slides", J of microscopy, 1970, 92(1):63-65.*
WHO "Preparation of 8-place slides for multiple testing in fluorescent antibody procedures", WHO, 1971, pp. 1-2.*
Rieder et al. "a comparison of fluorescence microscopy with the Ziehl-Neelsen technique in the examination of sputum for acid-fast bacilli", Int J Tuberc Lung Dis., 1999, 3(12):1101-1105.*
PCT International Search Report and Written Opinion, International Patent Application No. PCT/US2011/00002, dated Mar. 7, 2011.

* cited by examiner

*Primary Examiner* — Bin Shen
(74) *Attorney, Agent, or Firm* — McNees Wallace & Nurick LLC

(57) ABSTRACT

An apparatus and method for increasing the efficiency of finding a field of focus, and for increasing the accuracy of field of view in reading slides with fluorescent microscopy technology, including tuberculosis slides.

27 Claims, 5 Drawing Sheets

FLUORESCENT MARKED MICROSCOPE SLIDE

REFERENCE TO RELATED APPLICATIONS

This application claims priority to U.S. Provisional Patent Application No. 61/336,115, filed Jan. 15, 2010.

INTRODUCTION

The present teachings relate to a device and methodology for increasing the efficiency of finding a field of focus, and for increasing the accuracy of a field of view in reading slides with fluorescent microscopy technology.

Tuberculosis (TB) disease presents a global health problem. An estimated one-third of the world's population is infected with the causative agent of TB, *Mycobacterium tuberculosis*. While in most cases the disease remains latent, about 5 to 10% of persons infected will go on to develop active disease sometime in their life. Left undetected and/or untreated, patient mortality is about 50%. Furthermore, statistical studies show that an untreated infected individual will go on to infect 10 to 15 other individuals per annum.

The worldwide incidence of active TB has been on an increasing trend since at least 1990, when the World Health Organization began tracking incidence data. Estimates indicate that without an improvement in the current global TB situation, 150 million people will develop active tuberculosis and 36 million people will die by 2020. The global TB problem is further exacerbated by the increasing HIV epidemic. Persons with HIV who become infected with *Mycobacterium tuberculosis* also suffer from an increased risk of developing active TB. In fact, TB is the number one cause of death in HIV infected individuals.

Reducing the incidence of this disease is a global priority and is an integral part of the United Nations' Millennium Development Goals promulgated in 2000. In line with these goals, the World Health Organization (WHO) has developed the STOP TB Strategy, a multi-faceted approach for reducing the global burden of TB. The linchpin of this strategy is case detection through quality assured bacteriology. Specifically, a global target of greater than 70% smear positive case detection has been set.

Sputum smear bright field microscopy has been a mainstay in TB detection for a century and remains the most common case detection technique worldwide. This ubiquitous use is due in part to the fact that the procedure requires relatively few resources. This is especially important to developing countries, which are disproportionately burdened with TB (and HIV) relative to industrialized nations. Despite its role in TB healthcare, however, bright field microscopy suffers from low sensitivities of about 60%. In settings where HIV prevalence is high, sensitivities are significantly lower due to the frequently low bacillary loads often seen in HIV patients. Moreover, in laboratories where assay volumes are high, examination time may be attenuated, resulting in further loss of sensitivity.

The most common bright field sputum smear staining technique currently in use is the Ziehl-Neelsen (ZN) method, which employs a fuschin stain, acid-alcohol decolorizer, and a methylene blue counterstain. This and other staining methods take advantage of the "acid fastness" of *Mycobacterium tuberculosis* and other mycobacterial species, together known as acid fast bacilli (AFB). In these methods, the AFB take up stain but are recalcitrant to decolorization with acid, whereas common respiratory tract flora and debris destain. ZN staining results in AFB staining magenta against a blue background. With this technology, and with use of other bright field methods, it can be difficult to identify and distinguish the bacilli from the background material, and proper examination requires significant time from a skilled technician. Time and skill resources are often limited in many TB lab settings.

Based on the foregoing, the most widespread test for detecting tuberculosis is through bright field microscopic analysis utilizing white light from a standard optical microscope. The standard viewing power utilized for such detection is 1000×. However, because the morphology of the bacteria are unique and have a variety of distinguishing characteristics, and because of the difficulties with ZN staining referenced above, it takes a fairly sophisticated technician and/or lab expertise to detect tuberculosis. In addition, the standard and currently accepted testing parameters with bright field microscopy require one hundred separate "fields" of viewing at 1000× in order for a diagnosis to be made. This procedure is extremely time consuming and limits the number of slides a microscopist or technician can accurately read in a given day. Accordingly, there is a significantly greater demand for microscopists than is currently available. This is particularly true in parts of the world where tuberculosis tests are prominent and required, including Africa and Asia.

Fluorescent microscopy (FM) has also been shown to be useful for the detection of AFB. FM techniques make use of fluorescent dyes such as Auramine O, along with some form of decolorizer and quenching agent. With FM, AFB stain bright green to yellow against a dark background, resulting in a considerable distinction between the organism and the background compared to bright field methods. This increase in distinction reduces eye stress and permits the use of objectives with larger fields of view, thereby decreasing the total examination time. Altogether, FM based detection of TB has been proven to offer greater sensitivities and shorter examination times compared to standard bright field microscopy. Based on these advantages and the availability of new light emitting diode (LED) fluorescence microscopes, the World Health Organization has made a push towards the global utilization of fluorescence microscopy in order to diagnose tuberculosis.

Despite its recognized benefits, FM (both conventional and LED based) introduces significant problems that affect its utility and indication for widespread use. These problems center around the fact that FM is a dark field technique, and, as such, requires the sample to provide a light signal. In the case of TB smears, background fluorescence is quenched (important for increasing the signal to noise ratio). In samples where bacilli burden is low to non-existent, the examination field provides little to no signal on which to focus. Therefore, it becomes difficult to ensure the quality of assays where a negative result is found. Furthermore, the signal from fluorescently stained AFB is relatively low (compared to bright field methods) and can only be seen within a small number of focal planes. Here, inexperienced users can easily overlook positive samples by missing the focal planes where signal is distinguishable.

Fluorescence microscopes, then, require significantly greater training compared to bright field microscopes in order for microscopists to be familiar with finding a plane of focus. This is largely because the bright field technology also allows the microscopist to view non-AFB materials, including background material, which can also be more easily seen "above" and "below" the plane of focus.

Difficulty in focusing a fluorescence microscope is not only a problem for the inexperienced but is also a problem for the seasoned technician. As a result, it is very difficult for a microscopist to ascertain whether what he or she is viewing is in focus, and thus, the microscopist often does not have great confidence in reporting that there is no tuberculosis.

Finally, it remains very difficult for FM microscopists to ascertain whether they are looking at the same lateral field of view or new fields of view, especially when there is little to no background material to provide internal reference points when moving from field of view to field of view, and as a result, there is a lack of predictability in results, and a lower than desired level of accuracy in reading slides, even with the fluorescence microscopy technology.

In addition, FM has been unfeasible (and in some instances unsuitable) for most healthcare facilities around the world. This lack of feasibility is due to significant problems introduced by the technology, including: expensive capital costs; complex, short-lived and expensive light sources; technician fears of UV induced health hazards; notoriously delicate instrumentation; the need for stable power requirements; and significant training period requirements. Advances in light emitting diode (LED) technology have introduced bright, robust light sources powered with low voltage power supplies that can be used to replace conventional FM light sources, eliminating the aforementioned problems. In fact, manufacturers have introduced LED based attachments that can retrofit existing bright field microscopes to turn them into fluorescence microscopes. As with conventional FM, new LED FM technology has been shown to have increased TB detection sensitivity compared to bright field techniques. As stated above, those advances have resulted in the use of LED based FM being sanctioned by the WHO.

FM based technology will likely continue to be endorsed as the method of choice for TB detection by smear microscopy worldwide. Nonetheless, since FM implementation is being promoted worldwide, a mechanism to ensure that technicians are examining smears properly is critical for quality assured bacteriology.

Accordingly, there remains a demonstrated need in the art for a microscope reading technology that eliminates the stress of microscopists, increases the accuracy of readers' results, and increases the speed and efficiency with which slides may be read, including tuberculosis slides. There is a further need for a technology that allows fluorescent microscopy to be easily adapted and used, including in underdeveloped parts of the world, and areas where there is a high throughput of slides to be read.

SUMMARY

The present teachings provide a useful device comprising a microscopy slide imprinted with strategically placed ink that fluoresces such that when the slide is read with fluorescent microscopy technology, the pattern deposited on the slide enables a microscopist to find a field of focus and to accurately identify a field of view.

BRIEF DESCRIPTION OF THE DRAWINGS

The skilled artisan will understand that the drawings described below are for illustration purposes only. The drawings are not intended to limit the scope of the present teachings in any way.

DESCRIPTION OF VARIOUS EMBODIMENTS

Figure 1:
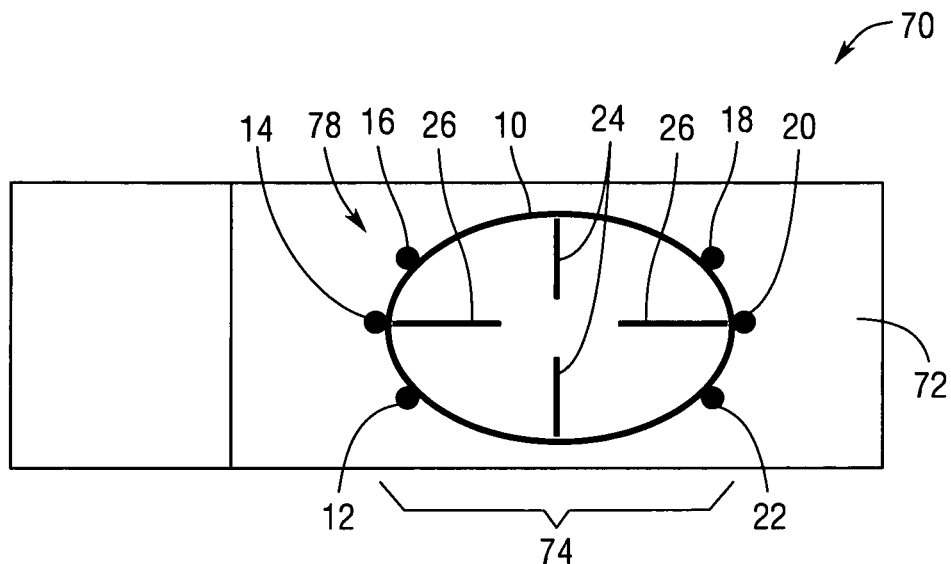
FIG. 1 depicts an embodiment of a fluorescent microscope slide having an elliptical design in accordance with the present teachings.

The fluorescent microscope slide 70 according to the present teachings comprises a microscope substrate 72 with markings 74 that fluoresce. The device enables microscopists to identify and maintain the proper focal plane for acid fast bacilli fluorescence microscopy. The microscope slide's 70 fluorescent demarcations or "markings" 74, which generally take the form of shapes, symbols, and the like, can be used for initial focusing and as focal guides throughout examination. These fluorescent landmarks can also be larger than the objective field of view so as to permit centering of the microscope over the focal point easily and without needing to find the landmark through the microscope ocular. Once centered over the landmark, a microscopist can adjust the focus until the fluorescent marking(s) 74 comes into focus. If the focal plane is not found, the microscopist can separate the slide and objective to a distance greater than the working distance of the objective, recheck the position of the objective relative to the fluorescent start point, and focus downward until the correct focal plane is found. The microscopist can then examine the specimen area. As fluorescent landmarks 74 are encountered during examination, the microscopist can determine the degree of focus and adjust as necessary.

The teachings herein demarcate for the microscopist the boundary of the sample area 78, which is important in training technicians how to ensure a "good prep" for the substrate. In the present case, a technician smears a specimen (e.g. from a patient) to completely fill the demarcated area, ensuring that enough specimen has been applied to the substrate 72. Boundary markings and markings within the boundary are visible through the specimen smear and provide a means to consistently gauge smear thickness by estimating the degree to which the markings 74 are covered. Proper smear amount and thickness are critical for ensuring the sensitivity of TB testing since thin, sparse specimens reduce the number of organisms available for identification. Current technologies do not provide a built in gauge for standard uniformity in slide preparation. Consequently, this impacts upon the reproducibility and uniformity of data that is generated through such slides. With the markings 74 of the fluorescent microscope slide 70, predictability in slide preparation is achieved, which increases the quality of test results and normalizes data.

Another feature of the fluorescent microscope slide 70 is that the demarcations allow a microscopist to establish a simple lateral coordinate system so that the microscopist can easily distinguish artifacts from important findings. This demarcation system allows one to review the same slide on multiple occasions and to reproduce the viewing results. Furthermore, the fluorescent findings can be more easily found during subsequent readings by a second party such as during a quality audit or a practical exam. This increases the quality control of tuberculosis slide reading and facilitates training. Such reproducibility is currently unavailable with existing technologies.

Another aspect of the fluorescent microscope slide 70 is that it enables microscopists, technicians, and other users to examine an appropriate amount of specimen. Here, landmarks that fluoresce 74 and are thus visible with dark field microscopy while viewing provide start and finish points that when traversed ensure that the correct number (or a desired number) of fields are examined.

In some embodiments, the fluorescent microscope slide 70 incorporates a consistent (or predetermined) location for the start of a microscopist's analysis. This provides the microscopist with a reproducible methodology for starting, progressing and stopping the reading, and allows for a standardized pattern of viewing across the slide. Because of the ability to initiate slide reading with a predictable methodology, the preset location enables the microscopist to cover larger viewing areas more efficiently and rapidly.

Because the process of reading slides can be physically and mentally exhausting on microscopists and other viewers, the existence of fluorescent demarcations 74 on the slide 70 also serves to reduce microscopist fatigue and therefore increases the accuracy of results. The psychological impact of the landmarks 74 reduces stress for the microscopist and actually provides an engineered incentive for the microscopist to finish the slide and focus on testing.

Another aspect of the fluorescent microscope slide 70 according to the teachings herein is to aid in specimen quantification. Landmarks 74 with fluorescent characteristics visible by dark field microscopy can demarcate known amounts of specimen area 78. These landmarks 74 enable the microscopist to accurately check separate fields with no overlap. (Overlap is experienced in teachings of the known art.) Due to the lack of overlap, there is much less risk of statistical variation, which allows for a more accurate average of cell samples per field. When using the markings 74 visible through the microscope ocular as the boundary in which to count, fluorescent object concentration can be determined.

The fluorescent microscope slide 70 according to the present teachings advantageously provides: (a) a fluorescence reference for determining whether or not a system is performing properly and (b) fluorescence calibration data. Landmarks of known or constant fluorescence value or landmarks with varying known fluorescence value on the same slide can be used to determine if the instrumentation and/or reagents are functioning correctly. Such landmarks 74 can also be used to generate a fluorescence standard curve. (Digital images or a light measuring device can also be employed for this purpose.)

The fluorescent microscope slide 70 according to the present teachings improves the accuracy and usability of slides. As a consequence, the device mitigates resistance in the field to the utilization of fluorescence microscope technology, increasing its acceptance by microscopists.

EXAMPLES

The device of the present teachings enables rapid and accurate detection of the presence of components of interest (e.g. acid fast bacilli) in a sample using fluoroscopic microscopy. The fluorescent microscope substrate 70 features a specimen receptacle (e.g. a microscope slide or cover) 72 comprising markings 74 on a surface of the receptacle that: fluoresce, demarcate a sample specimen area 78, identify examination start areas, and demarcate examination distances.

Stated otherwise, the fluorescent markings 74 define a target area 12 for a sample. In addition, fluorescent markings 74 about (i.e. proximate, adjacent to, or within) the target area 12 enable a microscopist or other user to ascertain a field of focus. Fluorescent markings 74 about the target area 12 also allow a user to identify a field of view.

Markings 74 of the fluorescent microscope slide 70 can assume any desired form including, but not limited to: lines, etchings, symbols, numbers, text, geometric shapes (e.g. ellipses 10, 30, 44, 50; circles 80; triangles 82; rectangles 76; diamonds 84; squares 88; trapezoids 86), or other distinctive configurations. Markings 74 can be of any size (e.g. width, height, or thickness) that accommodates an area considered statistically standard for AFB smears. As an example, markings 74 of the fluorescent microscope slide 70 can comprise a width of about 1.0 to 3.0 cm, a height of about 0.5 to 2.0 cm, and a thickness of about 0.01 to 0.2 cm. In some embodiments, markings 74 are flat or are generally flush with the microscope slide 70. In some embodiments, markings 74 are elevated above the microscope slide 70 or extend beyond the plane (or borders) thereof.

The microscope substrate 70 comprises a microscope specimen receptacle 72 such as a slide, a cover, or a combination thereof, fabricated from a material that permits viewing under a microscope. In some embodiments, a substrate is transparent and comprises a glass, plastic or silicon material. Contained on a surface of the receptacle 72, within or about the sample/specimen area 78, is a series of markings that have fluorescent qualities, such as paint, ink with fluorescent pigment or dye, autofluorescing ink, or etchings, that are formatted for a specific fluorescence application. Ink can be obtained from sources well known in the industry. One such example is Markem 4166 Series Ink combined with fluorescence pigment such as BASF Lumogen® F Yellow 083 or DayGlo Signal Green™ AX-18. Fluorescently marked slides can be fabricated using standard deposition techniques and/or glass printing procedures such as silk screen or pad printing.

The fluorescence intensity of paint can be modulated by adjusting the concentration of fluorescent pigment or dye or by cutting fluorescent paint with a non-fluorescent paint. Desired fluorescence intensity can be specific for each application. For example, in TB microscopy, fluorescence is minimized to prevent eye stress and fluorescence carryover in the specimen area, but is maintained bright enough to be clearly visible with standard fluorescence microscopy equipment.

To fabricate the fluorescent microscope slide 70, pigment, dye, or the like is added to ink in the appropriate ratio and mixed to a desired degree of homogeneity. Ink can be quality controlled by testing against fluorescence standards as needed. The fluorescent paint or ink can then be applied to a microscope specimen receptacle 72 using deposition or printing techniques known in the art such as pad or silk screen printing. Depending on the fluorescent substance or matrix used, heat or UV-light curing can be employed following deposition. In embodiments where fluorescent microscope slides 70 are printed or otherwise fabricated in the aggregate (e.g., in large sheets), the slides can then be cut to size.

As used herein, references to "horizontal" and "vertical" refer in direction as the viewer looks down on a slide in the orientation depicted in the Figures.

The markings 74 in FIG. 1 comprise a strategically sized elliptical shape 10 having approximately a 3 cm×2 cm×0.1 cm (width, height, and thickness, respectively) configuration. This ellipse 10 demarcates the area of specimen 78 that is considered statistically relevant for AFB smears. Embedded in the ellipse at strategically selected positions are target points, 12 through 22, of a diameter larger than the width of the ellipse line. These target areas 12 provide landmarks for finding an initial focus, as well as for defining an examination start point. Vertical lines 24 extend inside the ellipse from the top center and bottom center of ellipse 10, providing an intermediate focal checkpoint 24. Vertical lines 24 also mark the point at which 62.5 fields of view (from start points 16, 12, 18, or 20) were scanned when traveling horizontally and using a 100 power objective. Horizontal lines 26, initiating at circles 14 and 20, protrude into the ellipse 10, again defining an intermediate focal checkpoint 26 as well as marking 36.1 fields of view relative from start points 16 and 12 or 18 and 22, using a 100 power objective.

While the focal checkpoints 26 in FIG. 1 are lines, it will be understood that the fluorescent markings comprising checkpoints can assume any configuration capable of being oriented perpendicular to the direction of viewing.

Figure 2:
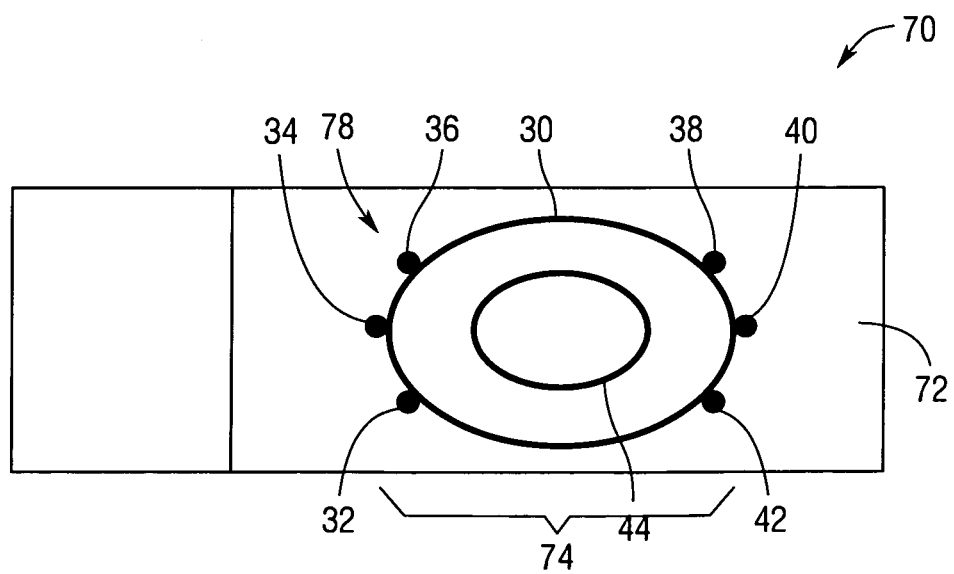
FIG. 2 shows an embodiment of a fluorescent microscope slide having an elliptical design in accordance with the present teachings.

FIG. 2 depicts a microscope slide 70 with another strategically sized elliptical shape 30, having approximately a 3 cm×2 cm×0.1 cm (width, height, and thickness, respectively) configuration. The outside ellipse 30 demarcates the area of specimen that is considered standard for AFB smears. Embedded in the ellipse at key positions are circles, 32 through 42, having a diameter larger than the ellipse line, which provide landmarks for finding an initial focus and for defining an examination start point. Centered inside ellipse 30 is a smaller concentric ellipse 44 of an approximately 2 cm×1 cm×0.05 cm (width, height, and thickness, respectively) configuration. This configuration is particularly suited for microscopists who desire to initiate the examination of smears at positions 34, 40, or on the top or bottom of ellipse 30. When starting from points 34 or 40 and moving horizontally, the first and second fluorescent demarcations 74 encountered in the field of view are 41.7 and 125 fields of view in a 100 power objective from start. When starting at the top or bottom of ellipse 30 and moving vertically into the ellipse, the first and second fluorescent demarcations 74 encountered in the field of view are 27.8 and 83.3 fields of view in a 100 power objective from start.

Figure 3:
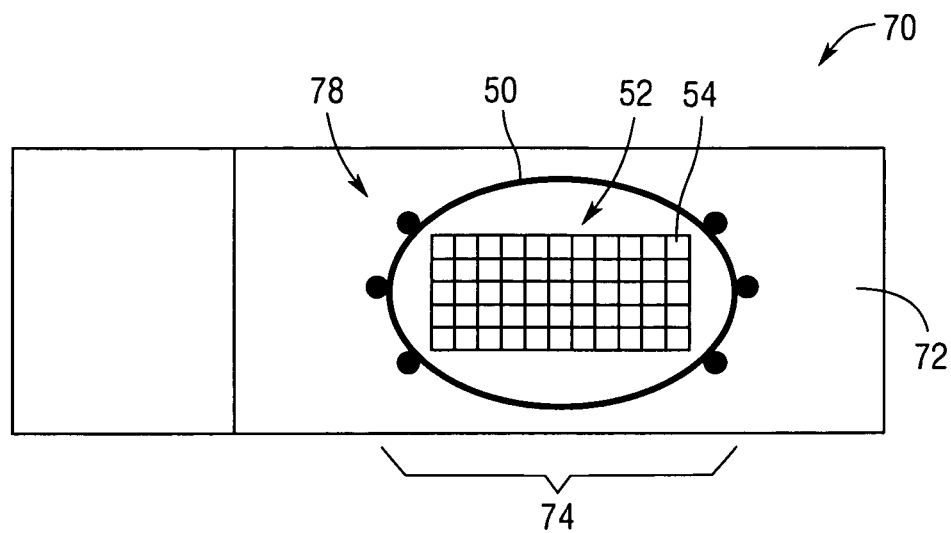
FIG. 3 is an embodiment of a fluorescent microscope slide having an elliptical design in accordance with the present teachings.

FIG. 3 depicts a microscope slide 70 with another strategically sized elliptical design 50, having an approximately 3 cm×2 cm×0.1 cm (width, height, and thickness, respectively) configuration. The outside ellipse 50 demarcates the area of specimen that is considered standard for AFB smears. Embedded in the ellipse is a rectangular grid 52. Each square, e.g., 54, defined within the grid 52 has an open area of approximately 0.18 cm×0.18 cm, for example, demarcated by fluorescent lines approximately 0.025 cm in width. Each dimension spans 10 fields of view and provides an area equivalent to 127 fields of view in a 100 power objective. To quantify bacilli load, then, a microscopist can scan the width of two squares for a total of 20 fields of view or the entirety of one square for a total of about 100 fields of view.

Figure 4:
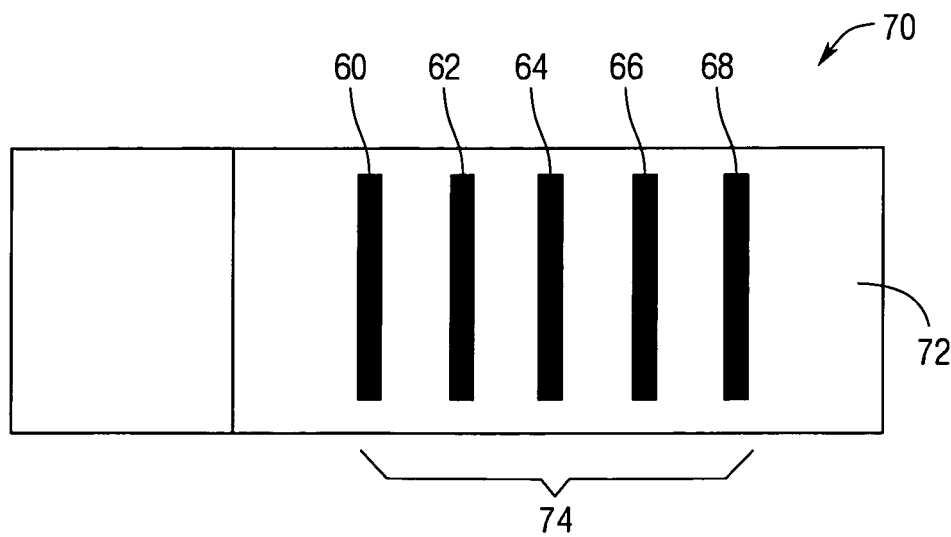
FIG. 4 depicts an embodiment of a fluorescent microscope slide having an elliptical design in accordance with the present teachings.
Figure 5:
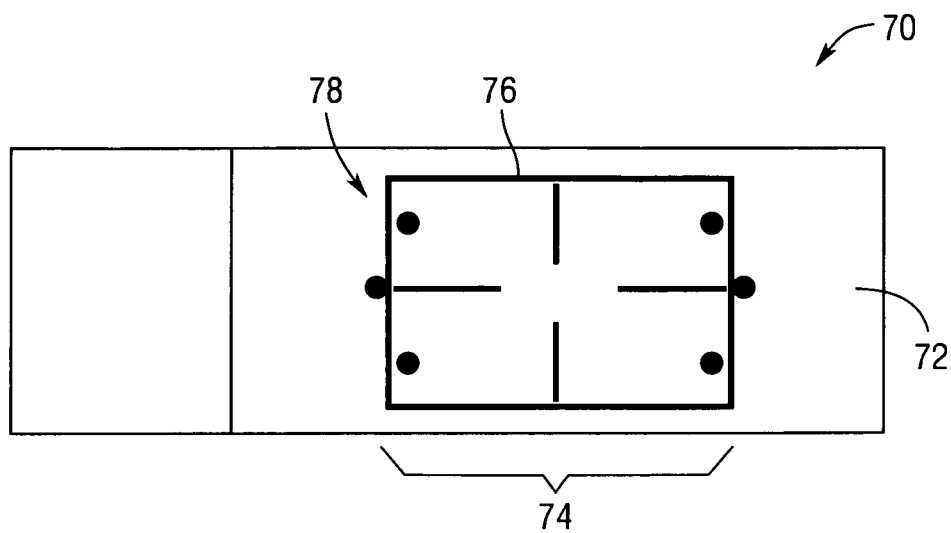
FIG. 5 shows an embodiment of a fluorescent microscope slide having a rectangular design in accordance with the present teachings.
Figure 6:
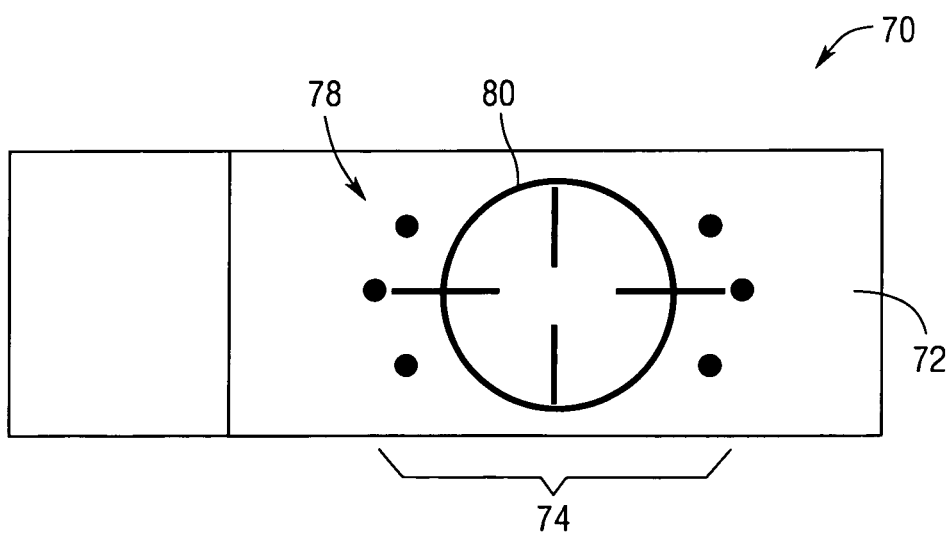
FIG. 6 is an embodiment of a fluorescent microscope slide having a circular design in accordance with the present teachings.
Figure 7:
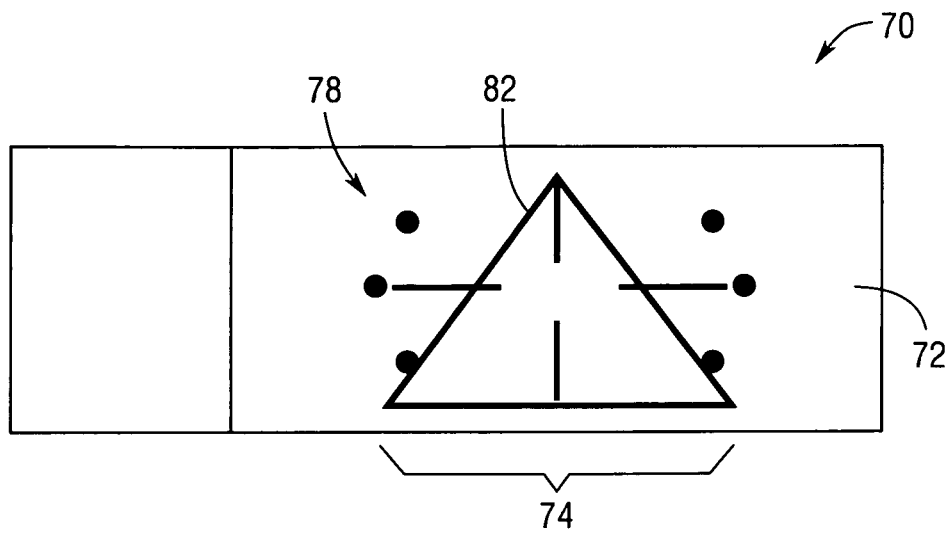
FIG. 7 depicts an embodiment of a fluorescent microscope slide having a triangular design in accordance with the present teachings.
Figure 8:
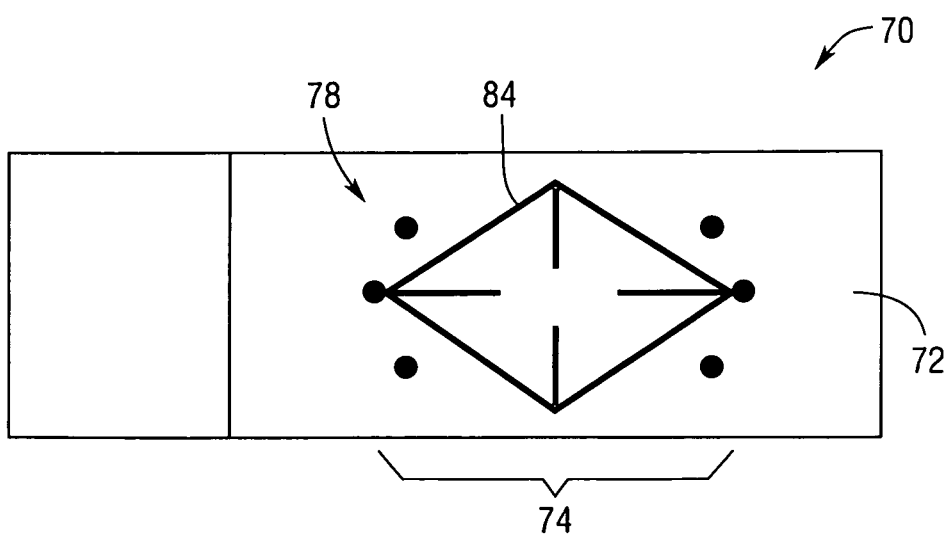
FIG. 8 shows an embodiment of a fluorescent microscope slide having a diamond design in accordance with the present teachings.
Figure 9:
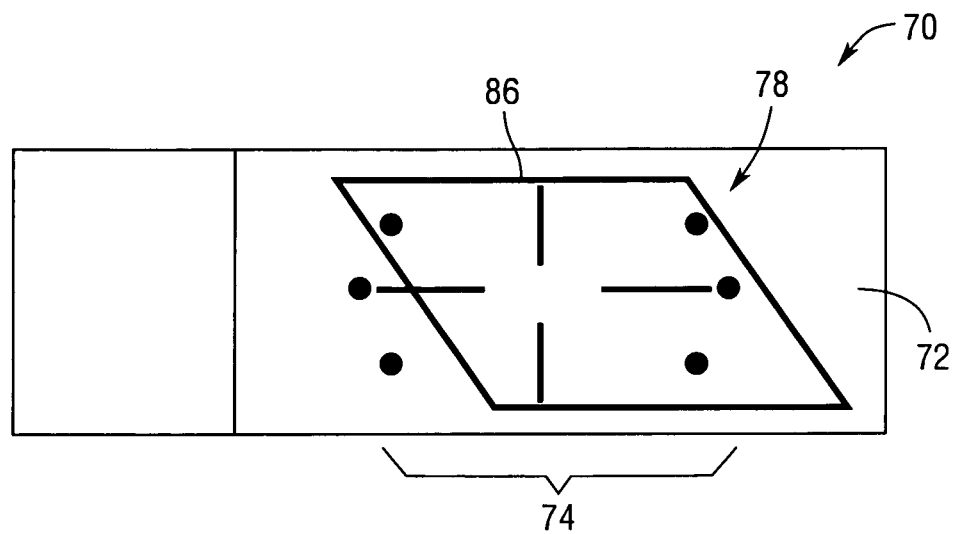
FIG. 9 is an embodiment of a fluorescent microscope slide having a trapezoidal design in accordance with the present teachings.
Figure 10:
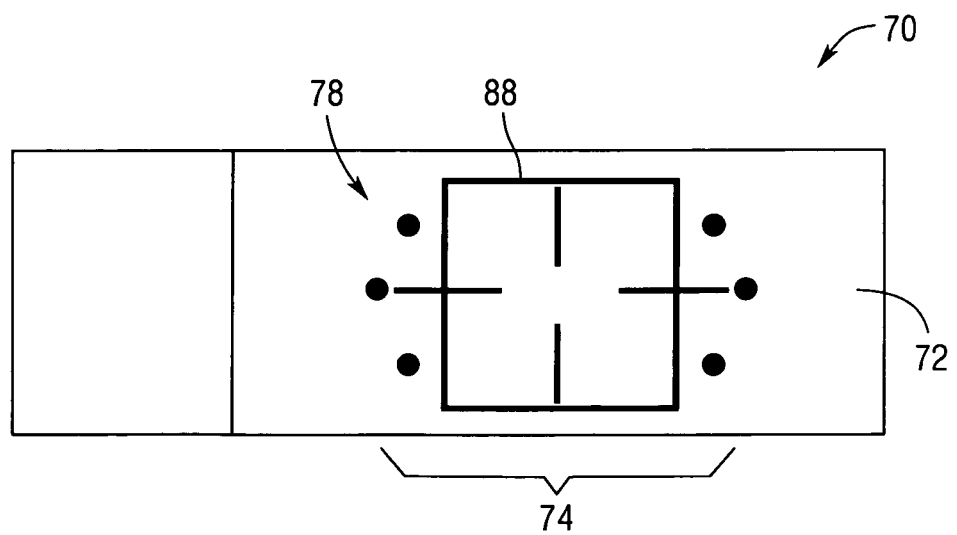
FIG. 10 depicts an embodiment of a fluorescent microscope slide having a square design in accordance with the present teachings.

FIG. 4 depicts a microscope slide with vertical lines, 60 through 68, approximately 0.2 cm in width. Each line contains a varying but known concentration of fluorescent pigment. Here lines A, B, C, D, and E have 0%, 0.0025%, 0.005%, 0.010%, and 0.015% w/w fluorescent pigment to ink, respectively. A fluorescence microscope equipped with a light measuring device, such as a digital camera, can be used to facilitate the capture of fluorescence from each line. Pixel counting software such as ImageJ can also be employed to expedite the measurement of fluorescence intensity.

The microscope slide 70 enables fluorescence calibration data to be generated by: calculating the concentration of pigment or dye in a sample; comparing the calculated concentration of sample pigment with known fluorescent intensity values of markings on the specimen receptacle 72; and generating a fluorescence intensity versus fluorescence pigment or dye concentration curve equation. Fluorescence concentration relative to pigment or dye concentration can also be calculated using the curve equation. In accordance with this calibration data and methodology, the fluorescence intensity of a sample component of interest can be ascertained. Moreover, the fluorescence of a specimen of unknown fluorescence concentration can be determined.

To demonstrate the quantification of fluorescence, a microscope slide 70 such as that shown in FIG. 4 was prepared by adding dye to ink in the ratios indicated above. The slide markings (lines) 74 were imaged using a microscope and digital imaging system comprising the following components: QBC ParaLens fluorescent microscope adapter; Nikon OptiPhot-2 microscope; Jenoptik ProgRes® digital camera; and a PC. Images were then analyzed with ImageJ by converting the images to grayscale. Pixel intensities were measured by defining a 200×200 pixel window and using ImageJ's "analyze" function. The following integrated densities were measured:

| Dye Concentration w/w | Integrated Density |
|---|---|
| 0.0000% | 1789217 |
| 0.0025% | 3998085 |
| 0.0050% | 5079408 |
| 0.0100% | 7499295 |
| 0.0150% | 7358896 |

Graphing the data demonstrates a linear relationship between dye concentration and pixel intensity up to 0.0100% dye, and fluorescence becomes saturated at 0.0150%. Regression analysis using the linear portion of data yields a least squares equation of $y=5.492\times10^8+2.189\times10^6$ with an $r^2$ value of 0.9761.

The present calibration data and methodology can also be used to test the quality and/or performance of articles such as the fluorescent microscope slide 70 herein, fluorescent microspheres, and other related articles. If desired, fluorescence calibration data can be employed to determine whether a fluorescence microscopy system is performing suitably or whether instrumentation and/or reagents are functioning correctly.

In the case of determining the quality of fluorescence microscope slides 70 (e.g. for TB smears) according to the present teachings, the calculated concentration of pigment in the smear slide lines can be compared directly to defined engineering specifications for said lines. For example, fluorescence intensity can be defined as 0.0100%±10% based on quantification against a standard curve as described herein. This, then, provides an efficient and convenient quality assurance mechanism for determining whether fluorescence microscope slides are suitable for market. In such case, an insert providing instructions for use can be included with articles of manufacture based on the fluorescent microscope slide 70.

The section headings used herein are for organizational purposes only and are not to be construed as limiting the subject matter described in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. A microscope substrate for use with a fluoroscopic microscopy system, comprising:
    a microscope specimen receptacle;
    fluorescent markings on a surface of the receptacle defining a target area for a sample;
    fluorescent markings on the surface of the receptacle about the target area demarcating a field of focus; and
    fluorescent markings on the surface of the receptacle about the target area identifying a field of view and wherein said fluorescent markings further comprise at least one intermediate focal checkpoint between the field of focus and the field of view having an orientation perpendicular to a direction of viewing.

2. The microscope substrate according to claim 1, wherein said fluorescent markings comprise landmarks for focal plane identification and maintenance.

3. The microscope substrate according to claim 1, wherein said fluorescent markings comprise landmarks having dimensions larger than a microscope objective field of view,
    said landmarks enabling a microscope to be centered over a focal point independent of a microscope ocular.

4. The microscope substrate according to claim 1, wherein said fluorescent markings comprise a lateral coordinate system for result reproducibility.

5. The microscope substrate according to claim 1, wherein said fluorescent markings further comprise start and end points which enable examination of a desired number of fields.

6. The microscope substrate according to claim 1, wherein said fluorescent markings comprise a configuration which accommodates a statistically relevant area of specimen for acid fast bacilli smears.

7. The microscope substrate according to claim 1, wherein said fluorescent markings comprise a planar configuration so as to be generally flush with the specimen receptacle.

8. The microscope substrate according to claim 1, wherein said fluorescent markings comprise lines, symbols, numbers, text, or geometric shapes.

9. The microscope substrate according to claim 8, wherein said geometric shapes comprise an elliptical, circular, triangular, rectangular, square, diamond, or trapezoidal configuration.

10. The microscope substrate according to claim 1, wherein said markings comprise a fluorescent pigment, dye, paint, ink, or autofluorescing ink.

11. A microscope substrate for use with a fluoroscopic microscopy system, comprising:
    a microscope specimen receptacle;
    fluorescent markings on a surface of the receptacle defining a sample specimen area;
    fluorescent markings on the surface of the receptacle about the sample specimen area demarcating a field of focus;
    fluorescent markings on the surface of the receptacle about the sample specimen area identifying a field of view and wherein said fluorescent markings further comprise at least one intermediate focal checkpoint between the field of focus and the field of view having an orientation perpendicular to a direction of viewing;
    fluorescent markings on the surface of the receptacle about the sample specimen area identifying an examination start point; and
    fluorescent markings on the surface of the receptacle about the sample specimen area demarcating an examination distance.

12. The microscope substrate according to claim 11, wherein said fluorescent markings comprise landmarks for focal plane identification and maintenance.

13. The microscope substrate according to claim 11, wherein said fluorescent markings comprise landmarks having dimensions larger than a microscope objective field of view,
    said landmarks enabling a microscope to be centered over a focal point independent of a microscope ocular.

14. The microscope substrate according to claim 11, wherein said fluorescent markings comprise a lateral coordinate system for result reproducibility.

15. The microscope substrate according to claim 11, wherein said fluorescent markings further comprise start and end points which enable examination of a desired number of fields.

16. The microscope substrate according to claim 11, wherein said fluorescent markings comprise a configuration which accommodates a statistically relevant area of specimen for acid fast bacilli smears.

17. The microscope substrate according to claim 11, wherein said fluorescent markings comprise a planar configuration so as to be generally flush with the specimen receptacle.

18. The microscope substrate according to claim 11, wherein said fluorescent markings comprise lines, symbols, numbers, text, or geometric shapes.

19. The microscope substrate according to claim 18, wherein said geometric shapes comprise an elliptical, circular, triangular, rectangular, square, diamond, or trapezoidal configuration.

20. The microscope substrate according to claim 11, wherein said markings comprise a fluorescent pigment, dye, paint, ink, or autofluorescing ink.

21. A microscope substrate for detecting the presence of acid fast bacilli using fluoroscopic microscopy, comprising:
    a microscope specimen receptacle;
    fluorescent markings on a surface of the receptacle defining a target area for a sample;
    fluorescent markings on the surface of the receptacle about the target area demarcating a field of focus;
    fluorescent markings on the surface of the receptacle about the target area identifying a field of view and wherein said fluorescent markings further comprise at least one intermediate focal checkpoint between the field of focus and the field of view having an orientation perpendicular to a direction of viewing; and
    wherein said fluorescent markings comprise a configuration which accommodates a statistically relevant area of specimen for acid fast bacilli smears.

22. A method for examining a sample using a fluorescence microscope substrate, comprising:
    preparing a microscope specimen receptacle having fluorescent markings on a surface of the receptacle defining a target area for a sample, having fluorescent markings on the surface of the receptacle about the target area demarcating a field of focus, and having fluorescent markings on the surface of the receptacle about the target area identifying a field of view, wherein said fluorescent markings further comprise at least one intermediate focal checkpoint between the field of focus and the field of view having an orientation perpendicular to a direction of viewing;

viewing the fluorescent markings of said specimen receptacle under fluoroscopic microscope;

identifying a focal plane; and examining the sample.

23. The method of claim 22, wherein identifying said focal plane further comprises:

separating the microscope specimen receptacle and a microscope objective to a distance greater than a working distance of said objective; and viewing a position of the objective relative to a fluorescent start point until a correct focal plane is found.

24. The method of claim 22, further comprising determining cell sample concentration by:

employing fluorescent markings on said microscope specimen receptacle for demarcating known amounts of a sample area and separate fields; and using fluorescent markings visible through a microscope ocular as a boundary for counting cell samples per field.

25. The method of claim 22, further comprising generating fluorescence calibration data by:

calculating a concentration of pigment in a sample;

comparing the calculated concentration of sample pigment with known fluorescent intensity values of fluorescent markings on said microscope specimen receptacle; and generating a fluorescence intensity versus fluorescence pigment concentration curve equation.

26. The method of claim 25, further comprising using said fluorescence calibration data for calculating fluorescence intensity of a sample component of interest.

27. The method of claim 25, further comprising using generated fluorescence calibration data for determining whether a fluorescence microscopy system is performing suitably or whether instrumentation and reagents are functioning appropriately.

* * * * *